US011053227B2

(12) United States Patent
Colli et al.

(10) Patent No.: US 11,053,227 B2
(45) Date of Patent: Jul. 6, 2021

(54) PROCESS FOR PREPARING INTERMEDIATES FOR THE SYNTHESIS OF OPTICALLY ACTIVE BETA-AMINO ALCOHOLS BY ENZYMATIC REDUCTION AND NOVEL SYNTHESIS INTERMEDIATES

(71) Applicant: OLON S.P.A., Rodano (IT)

(72) Inventors: Corrado Colli, Rodano (IT); Giorgio Bertolini, Rodano (IT); Mara Sada, Rodano (IT); Faris Garis, Rodano (IT); Filippo Nisic, Milan (IT); Aldo Bianchi, Solara (IT); Cinzia Biaggi, Segrate (IT); Romano Di Fabio, Milan (IT); Silvano Ronzoni, Milan (IT); Stefania Bertuolo, Milan (IT); Adolfo Prandi, Zelo Buon Persico (IT); Stefano Maiorana, Milan (IT)

(73) Assignee: OLON S.P.A., Rodano (IT)

( * ) Notice: Subject to any disclaimer, the term of this patent is extended or adjusted under 35 U.S.C. 154(b) by 0 days.

(21) Appl. No.: 16/954,704

(22) PCT Filed: Dec. 19, 2018

(86) PCT No.: PCT/IB2018/060335
§ 371 (c)(1),
(2) Date: Jun. 17, 2020

(87) PCT Pub. No.: WO2019/123311
PCT Pub. Date: Jun. 27, 2019

(65) Prior Publication Data
US 2020/0385366 A1 Dec. 10, 2020

(30) Foreign Application Priority Data
Dec. 20, 2017 (IT) .................. 102017000147611

(51) Int. Cl.
*C07D 405/06* (2006.01)
*C07D 207/408* (2006.01)
*C12P 13/02* (2006.01)

(52) U.S. Cl.
CPC ....... *C07D 405/06* (2013.01); *C07D 207/408* (2013.01); *C12P 13/02* (2013.01); *C07B 2200/07* (2013.01)

(58) Field of Classification Search
CPC .................. C07D 405/06; C07D 207/408
See application file for complete search history.

(56) References Cited

U.S. PATENT DOCUMENTS 6,355,664 B1 * 3/2002 Kelly .................. C07D 207/40
514/389

FOREIGN PATENT DOCUMENTS

WO   2009/040080   4/2009
WO   2017001907    5/2017

OTHER PUBLICATIONS

Italian Priority document issued by the EPO dated Oct. 9, 2018 for IT application No. 11201700147611.
International Search Report issued by the EPO dated Apr. 30, 2019 for PCT/EP2018/060335.
International Preliminaty Report on Patentability issued by the EPO dated Jun. 23, 2020 for PCT/EP2018/060335.
Database WPI Week 199418 Thomson Sci enti ti c, London, GB; AN 1994-147902—XP002785425, & JP H06 92920 A (Kawaken Fin E Chem Co Ltd) Apr. 5, 1994 (Apr. 5, 1994).
Izumi, T. et al.: "Baker's Yeast Reducti on of alpha-(Alkoxycarbonylamino)acetophenones and Lipase-Catal ysed Resolution of 2-(Alkoxycarbonylamino)-1-arylethanols ", Journal of Chemical Technology and Biotech nology, vol. 66, No. 3, Jul. 1996 (Jul. 1996), pp. 233-242, XP002785426.
Tanielyan, S.K. et al : "Two Efficient Enantioselective Syntheses of 2-Amino-1-phenylethanol", Organi c Process Resea RCH & Developm ent, vol. 10, No. 5, Aug. 11, 2006 (Aug. 11, 2006), pp. 393-898, XP002798466, abstract p. 895, col. 2, line 1—p. 897, col. 1, line 13; compounds 7-9 equation 2.
T.W. Greene, John Wiley & Sons, Ltd, "Protective Groups in Organic Synthesis", 5th edition, 2014 (summary).

* cited by examiner

*Primary Examiner* — Golam M Shameem
(74) *Attorney, Agent, or Firm* — Silvia Salvadori

(57) ABSTRACT

Subject-matter of the present invention is a process for preparing intermediates for the synthesis of optically active beta-amino alcohols by enzymatic reduction of the corresponding beta-amino ketones. Subject-matter of the invention are also said novel synthesis intermediates and the use thereof in the preparation of active pharmaceutical ingredients, among which vilanterol and the salts thereof.

5 Claims, No Drawings
Specification includes a Sequence Listing.

SEQUENCE LISTING

```
<160> NUMBER OF SEQ ID NOS: 2

<210> SEQ ID NO 1
<211> LENGTH: 250
<212> TYPE: PRT
<213> ORGANISM: Geobacillus thermodenitrificans

<400> SEQUENCE: 1

Met Arg Leu Lys Gly Lys Ala Ala Ile Val Thr Gly Gly Ala Ser Gly
1               5                   10                  15

Ile Gly Arg Ala Thr Ala Ile Arg Phe Ala Glu Glu Gly Ala Lys Val
            20                  25                  30

Ala Val Ser Asp Ile Asn Glu Glu Gly Glu Glu Thr Val Arg Leu
        35                  40                  45

Ile Arg Glu Lys Gly Gly Glu Ala Ile Phe Val Gln Thr Asp Val Ala
    50                  55                  60

Asp Ser Lys Gln Val Ser Arg Leu Val Gln Thr Ala Val Asp Ala Phe
65                  70                  75                  80

Gly Gly Leu His Ile Leu Phe Asn Asn Ala Gly Ile Gly His Ser Glu
                85                  90                  95

Val Arg Ser Thr Asp Leu Ser Glu Glu Glu Trp Asp Arg Val Ile Asn
            100                 105                 110

Val Asn Leu Lys Gly Val Phe Leu Gly Ile Lys Tyr Ala Val Pro Val
            115                 120                 125

Met Lys Gln Cys Gly Gly Gly Ala Ile Val Asn Thr Ser Ser Leu Leu
    130                 135                 140

Gly Ile Lys Gly Lys Lys Tyr Glu Ser Ala Tyr Asn Ala Ser Lys Ala
145                 150                 155                 160

Gly Val Ile Leu Leu Thr Lys Asn Ala Ala Leu Glu Tyr Gly Lys Phe
                165                 170                 175

Asn Ile Arg Val Asn Ala Ile Ala Pro Gly Val Ile Asp Thr Asn Ile
            180                 185                 190
```

```
Ile Thr Pro Trp Lys Gln Asp Glu Arg Lys Trp Pro Ile Ile Ser Lys
        195                 200                 205

Ala Asn Ala Leu Gly Arg Ile Gly Thr Pro Glu Val Ala Asn Ala
    210                 215                 220

Val Leu Phe Leu Ala Ser Asp Glu Ala Ser Phe Ile Thr Gly Ala Thr
225                 230                 235                 240

Leu Ser Val Asp Gly Gly Leu Thr Phe
                245                 250

<210> SEQ ID NO 2
<211> LENGTH: 241
<212> TYPE: PRT
<213> ORGANISM: Candida magnoliae

<400> SEQUENCE: 2

Met Thr Thr Thr Ser Asn Ala Leu Val Thr Gly Gly Ser Arg Gly Ile
1               5                   10                  15

Gly Ala Ala Ser Ala Ile Lys Leu Ala Gln Glu Gly Tyr Asn Val Thr
                20                  25                  30

Leu Ala Ser Arg Ser Val Asp Lys Leu Asn Glu Val Lys Ala Lys Leu
            35                  40                  45

Pro Ile Val Gln Asp Gly Gln Lys His Tyr Ile Trp Glu Leu Asp Leu
    50                  55                  60

Ala Asp Val Glu Ala Ala Ser Ser Phe Lys Gly Ala Pro Leu Pro Ala
65                  70                  75                  80

Arg Ser Tyr Asp Val Phe Val Ser Asn Ala Gly Val Ala Ala Phe Ser
                85                  90                  95

Pro Thr Ala Asp His Asp Asp Lys Glu Trp Gln Asn Leu Leu Ala Val
            100                 105                 110

Asn Leu Ser Ser Pro Ile Ala Leu Thr Lys Ala Leu Leu Lys Asp Val
            115                 120                 125

Ser Glu Arg Pro Val Asp Lys Pro Leu Gln Ile Ile Tyr Ile Ser Ser
    130                 135                 140

Val Ala Gly Leu His Gly Ala Ala Gln Val Ala Val Tyr Ser Ala Ser
145                 150                 155                 160

Lys Ala Gly Leu Asp Gly Phe Met Arg Ser Val Ala Arg Glu Val Gly
                165                 170                 175

Pro Lys Gly Ile His Val Asn Ser Ile Asn Pro Gly Tyr Thr Lys Thr
            180                 185                 190

Glu Met Thr Ala Gly Ile Glu Ala Leu Pro Asp Leu Pro Ile Lys Gly
    195                 200                 205

Trp Ile Glu Pro Glu Ala Ile Ala Asp Ala Val Leu Phe Leu Ala Lys
    210                 215                 220

Ser Lys Asn Ile Thr Gly Thr Asn Ile Val Val Asp Asn Gly Leu Ile
225                 230                 235                 240

Ala
```

PROCESS FOR PREPARING INTERMEDIATES FOR THE SYNTHESIS OF OPTICALLY ACTIVE BETA-AMINO ALCOHOLS BY ENZYMATIC REDUCTION AND NOVEL SYNTHESIS INTERMEDIATES

This application is a U.S. national stage of PCT/IB2018/060335 filed on 19 Dec. 2018, which claims priority to and the benefit of Italian Patent Application No. 102017000147611 filed 20 Dec. 2017, the contents of which are incorporated herein by reference in their entireties.

A subject-matter of the present invention is a process for preparing intermediates for the synthesis of optically active beta-amino alcohols by enzymatic reduction of the corresponding beta-amino ketones. Subject-matter of the invention are also said novel synthesis intermediates and the use thereof in the preparation of active pharmaceutical ingredients, among which vilanterol and the salts thereof.

TECHNICAL FIELD

Amino alcohols, in particular chiral phenyl-beta-amino alcohols are very important synthons for the synthesis of active pharmaceutical ingredients; their basic structure is for example present in the hormones adrenalin and nor-adrenalin, in the drugs used for to treat cardiac problems, for example sotalol and arbutamine, in those used for treating asthma or chronic obstructive pulmonary disease (COPD) such as vilanterol, salbutamol, colterol, isoproterenole, and in different natural products such as for example the natural antiviral product (+) tembamide.

Optically active beta-amino alcohols are also of industrial interest as they can be used as chiral ligands or auxiliaries in different types of asymmetric syntheses.

Given the importance of such molecules, a number of synthesis methods have been developed over the years.

Initially the most used synthesis path, as it is promising in terms of optical purity, was the chiral resolution by optically active chemical compounds of the racemic amino alcohol but unfortunately such a synthesis path was not convenient in terms of yield.

Recently different enantioselective synthesis methods have been developed, that are more effective than the resolution, in terms of yield. For example, methods that are based on the chemical reduction of ketones and methods based on the hydrogenation in the presence of stereoselective catalysts and ligands are known.

The enantioselective reductions of chemical type imply the use of potentially hazardous reagents, very expensive ligands and in general do not yield to alcohols with enantiomeric excess higher than 97-98%. Therefore the raw compounds obtained need a subsequent purification.

The hydrogenation often involves the use of high pressures, expensive metal catalysts and often yields to impurities due to an excessive reduction ("overreduction") or to secondary reactions on other parts of the molecule.

The use of biochemical agents able to reduce carbonyl groups to hydroxy groups is also known. Among the biochemical methods the most used in this type of reaction is the use of yeasts. However, their use brings to many disadvantages such as the difficult reproducibility of the results over time because of the proliferation of hybrid breeds of yeast which tend to progressively change, because of the need of very high dilutions and the difficult collection of the desired product due to the presence of high amounts of biomasses.

Another biochemical method provides for the use of enzymes for the enantioselective reduction of carbonyl groups in particular of alpha halogen-ketones, as described in the Application WO2017/001907. This method provides for the reduction of a halogen ketone to halogen alcohol, followed by an alkylation with an amine, to yield the desired amino alcohol. The disadvantage is that, in the presence of an amine (base), the halogen alcohol tends to give the corresponding epoxide, which, in the presence of the amine itself, is opened in the 1 and 2 positions with low selectivity, bringing to the formation of by-products.

Reaction Scheme:

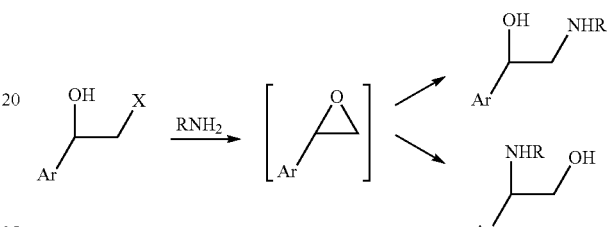

For this reason, in the procedure used in WO2017/001907, at the end of the enzymatic reduction, the benzyl OH is protected, for being deprotected after the alkylation of the amine.

With the aim of solving the problems above, the Applicant tried the direct enzymatic reduction of beta-amino ketones to beta-amino alcohols, so as to have the amine group already introduced in the desired position. However the use of enzymes on this type of substrates showed considerable difficulties and it was not possible to effectively carry out the reduction.

OBJECTS OF THE INVENTION

It is an object of the invention to provide a process suitable for preparing intermediates for the synthesis of optically active beta-amino alcohols, with good yields and high enantiomeric excesses even on industrial scale.

It is another object of the invention to provide an enzymatic process suitable for preparing intermediates for the synthesis of optically active beta-amino alcohols, that overcomes the disadvantages of the prior art.

It is a further object of the invention to provide novel intermediates useful in particular, but not only, for preparing vilanterol, adrenalin, noradrenalin, R-salbutamol, R-colterol, R-isoproterenole, (−)-arbutamine and the salts thereof.

DESCRIPTION OF THE INVENTION

The Applicant has surprisingly found that, by using a beta-amino ketone wherein the amine group has lost its basicity, for example by transforming to an amide, imide or carbamate group, it is possible to carry out its enzymatic reduction and obtain optically active amino-alcohols, with high yields and purities.

Thus, according to one of its aspects, subject-matter of the invention is a process for preparing an optically active compound of Formula (I)

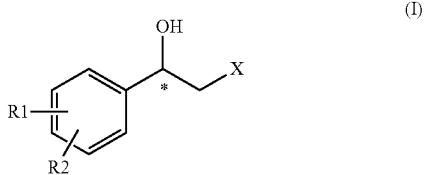

wherein
the asterisk indicates the chiral carbon is in the (S) form or (R) form;
X represents an amide, imide or carbamate residue bound to the compound of formula (I) through the nitrogen atom;
$R_1$ and $R_2$ are independently selected from hydrogen, —OPr, —CH$_2$OPr, —OH, —CH$_2$OH and $C_1$-$C_4$-alkoxy; wherein Pr is a hydroxy protective group and, when two Pr protective groups are in the compound of formula (I):
said two Pr protective groups can be the same or different from one another; or
said two Pr protective groups, together with the oxygen atoms to which they are bound, may form a cycle fused with the benzene;
said process comprising the enzymatic reduction of the compound of Formula (II)

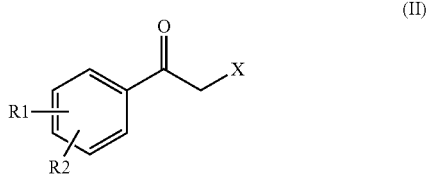

wherein X, $R_1$ and $R_2$ are as defined above.
According to a preferred embodiment, the compound of Formula (I) is a compound of Formula (I')

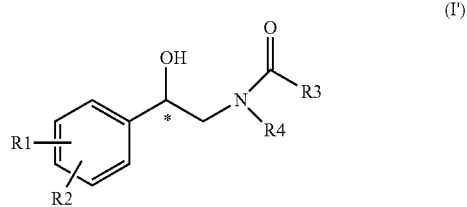

wherein
the asterisk, $R_1$ and $R_2$ are as defined above;
$R_3$ is selected from an hydrogen, alkyl, alkoxy, aryl, alkylaryl and arylalkyl;
$R_4$ is selected from hydrogen, alkyl, aryl, alkylaryl and arylalkyl;
or else
$R_3$ and $R_4$, together with the carboxamide group (HN—C=O) bonding them, constitute an imide.
The expression "chiral carbon is in the (S) form or in the (R) form" herein means that at least 80%, preferably at least 90-95%, more preferably 98-99.9% of the compound of Formula (I) and (I') is in said configuration.

According to a preferred embodiment, the chiral carbon of the compound of Formula (I) and (I') is in the (R) configuration.

The term "alkyl" herein means a saturated, linear or branched, alkyl residue, preferably having 1 to 6 carbon atoms, advantageously 1 to 4 carbon atoms, for example the methyl or ethyl group.

The term "alkoxy" herein means a saturated, linear or branched, alkoxy residue, preferably having 1 to 6 carbon atoms, advantageously 1 to 4 carbon atoms, for example the methyl or ethyl group.

The term "aryl" herein means an aromatic hydrocarbon residue, preferably selected from phenyl and naphthyl.

The term "alkylaryl" herein means an aromatic hydrocarbon residue, preferably selected from phenyl and naphthyl, substituted with one or more alkyls, as defined above.

The term "arylalkyl" herein means a saturated, linear or branched, alkyl residue, preferably having 1 to 6 carbon atoms, advantageously 1 to 4 carbon atoms as defined above, substituted with one or more aryls, as defined above.

The expression "hydroxy protective group" means any protective group able to protect the hydroxy function without interfering with the reduction reaction. Such groups can be for example selected from those mentioned in T. W. Greene, John Wiley & Sons, Ltd, "*Protective Groups in Organic Synthesis*", 5th edition, 2014. According to a preferred embodiment of the invention, the —OPr groups, as defined above, include esters and acetonides.

Other protective groups according to the present invention include the silanes, for example the silyl group; alternatively, when there are two Pr groups, said silane protective groups, together with the two oxygen atoms to which they are bound, may form a cycle fused with the benzene.

According to another embodiment, when the groups $R_1$ and $R_2$ are on adjacent carbon atoms and there are two Pr groups, said two Pr groups represent a carbonyl group (=CO) bound to the two oxygen atoms.

According to a preferred embodiment, $R_1$ and $R_2$ are both —OH or OPr, wherein the Pr groups can be the same or different from one another, preferably the same.

According to another preferred embodiment, one of $R_1$ and $R_2$ is OH or —OPr and the other is —CH$_2$OH or —CH$_2$OPr.

According to another embodiment, $R_1$ and $R_2$ are different from hydrogen and are on adjacent positions on the benzene ring, preferably in the 3 and 4 positions of the benzene ring.

According to another preferred embodiment, when $R_1$ and $R_2$ are each independently —OPr or —CH$_2$OPr, they form a cycle fused with the benzene ring; in this case, according to a more preferred embodiment, they are on adjacent positions of the benzene ring.

According to a preferred embodiment, $R_3$ is hydrogen, saturated and linear $C_1$-$C_6$ alkyl, preferably methyl or ethyl and $R_4$ is hydrogen or methyl.

According to another preferred embodiment, $R_3$ and $R_4$, together with the carboxamide group bonding them, represent a succinimide or a phthalimide possibly substituted, advantageously the succinimide or substituted succinimide, for example with one or more fluorine atoms.

Preferred compounds of Formula (II) are selected from the following:

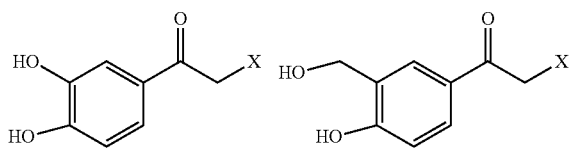
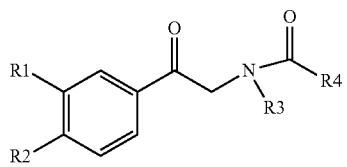
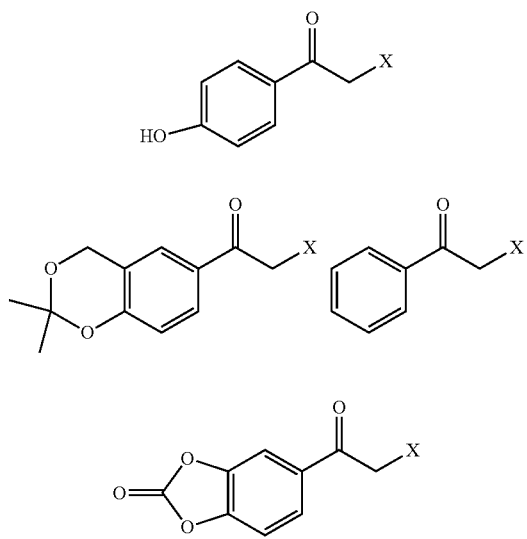

wherein X is a substituent selected from

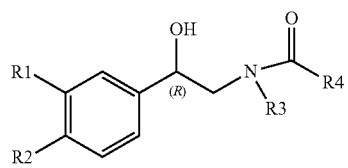

wherein ALK represents an alkyl as defined above, advantageously methyl or ethyl, said substituent X being bound to the molecule through the nitrogen atom, as depicted by the dashed line.

According to a particularly preferred embodiment, subject-matter of the invention is a process for preparing an optically active compound of Formula (I")

(I")

wherein
the asterisk, $R_1$ and $R_2$ are as defined above;
$R_3$ and $R_4$, together with the carboxamide group (HN—C=O) bonding them, constitute an imide, said process comprising the enzymatic reduction of the compound of Formula (II")

(II")

wherein $R_1$, $R_2$, $R_3$ and $R_4$ are as defined above.

According to the last embodiment, preferably the Pr groups form a cycle fused with the benzene, advantageously having the following formula:

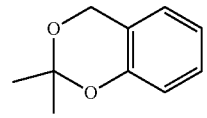

Still according to the last embodiment, preferably said imide is succinimide.

The compounds of Formula (II) and (II") can be easily prepared according to the methods known in the art.

The process of the invention preferably uses at least one oxidoreductase enzyme, which is preferably a polypeptide originating from yeasts or bacteria, advantageously from bacteria.

The enantioselective enzymatic reduction can be carried out by using the oxidoreductase enzyme in suspension in a reaction mixture, or immobilized according to known techniques. The enzyme can be purified, only partially purified, or can be contained in cells. The cells themselves can be in a native state, in a permeabilized state or in a lysed state. Preferably, the enzyme is expressed in *E. coli* and used as a suspension of native cells.

According to a preferred embodiment, said enzymatic reduction is carried out with at least one oxidoreductase enzyme, in the presence of at least one cofactor and at least one co-substrate that regenerates said cofactor.

The process of enzymatic reduction of the compounds of Formula (II) or (II") can be carried out for example in a reaction mixture comprising said compound of Formula (II), an oxidoreductase enzyme, NADH or NADPH as cofactor, a co-substrate.

According to a preferred embodiment, said at least one oxidoreductase enzyme that is used in the process of the invention, has a sequence selected from the sequences SEQ ID No: 1, herein below also indicated as "OX 56", described in EP1963516 (IEP) and SEQ ID No.: 2 herein below also indicated as "OX 62", described in EP1929001 (BASF).

According to a more preferred embodiment, said at least one oxidoreductase enzyme that is used in the process of the invention has the sequence SEQ ID No: 1.

The sequences are described in the sequence listing herein attached and depicted below:

SEQ ID NO. 1
Met Arg Leu Lys Gly Lys Ala Ala Ile Val Thr Gly
Gly Ala Ser Gly Ile Gly Arg Ala Thr Ala Ile Arg

-continued

Phe Ala Glu Glu Gly Ala Lys Val Ala Val Ser Asp

Ile Asn Glu Glu Gly Gly Glu Glu Thr Val Arg Leu

Ile Arg Glu Lys Gly Gly Glu Ala Ile Phe Val Gln

Thr Asp Val Ala Asp Ser Lys Gln Val Ser Arg Leu

Val Gln Thr Ala Val Asp Ala Phe Gly Gly Leu His

Ile Leu Phe Asn Asn Ala Gly Ile Gly His Ser Glu

Val Arg Ser Thr Asp Leu Ser Glu Glu Glu Trp Asp

Arg Val Ile Asn Val Asn Leu Lys Gly Val Phe Leu

Gly Ile Lys Tyr Ala Val Pro Val Met Lys Gln Cys

Gly Gly Gly Ala Ile Val Asn Thr Ser Ser Leu Leu

Gly Ile Lys Gly Lys Lys Tyr Glu Ser Ala Tyr Asn

Ala Ser Lys Ala Gly Val Ile Leu Leu Thr Lys Asn

Ala Ala Leu Glu Tyr Gly Lys Phe Asn Ile Arg Val

Asn Ala Ile Ala Pro Gly Val Ile Asp Thr Asn Ile

Ile Thr Pro Trp Lys Gln Asp Glu Arg Lys Trp Pro

Ile Ile Ser Lys Ala Asn Ala Leu Gly Arg Ile Gly

Thr Pro Glu Glu Val Ala Asn Ala Val Leu Phe Leu

Ala Ser Asp Glu Ala Ser Phe Ile Thr Gly Ala Thr

Leu Ser Val Asp Gly Gly Gly Leu Thr Phe

SEQ ID No. 2

Met Thr Thr Thr Ser Asn Ala Leu Val Thr Gly Gly

Ser Arg Gly Ile Gly Ala Ala Ser Ala Ile Lys Leu

Ala Gln Glu Gly Tyr Asn Val Thr Leu Ala Ser Arg

Ser Val Asp Lys Leu Asn Glu Val Lys Ala Lys Leu

Pro Ile Val Gln Asp Gly Gln Lys His Tyr Ile Trp

Glu Leu Asp Leu Ala Asp Val Glu Ala Ala Ser Ser

Phe Lys Gly Ala Pro Leu Pro Ala Arg Ser Tyr Asp

Val Phe Val Ser Asn Ala Gly Val Ala Ala Phe Ser

Pro Thr Ala Asp His Asp Asp Lys Glu Trp Gln Asn

Leu Leu Ala Val Asn Leu Ser Ser Pro Ile Ala Leu

Thr Lys Ala Leu Leu Lys Asp Val Ser Glu Arg Pro

Val Asp Lys Pro Leu Gln Ile Ile Tyr Ile Ser Ser

Val Ala Gly Leu His Gly Ala Ala Gln Val Ala Val

Tyr Ser Ala Ser Lys Ala Gly Leu Asp Gly Phe Met

Arg Ser Val Ala Arg Glu Val Gly Pro Lys Gly Ile

His Val Asn Ser Ile Asn Pro Gly Tyr Thr Lys Thr

Glu Met Thr Ala Gly Ile Glu Ala Leu Pro Asp Leu

Pro Ile Lys Gly Trp Ile Glu Pro Glu Ala Ile Ala

Asp Ala Val Leu Phe Leu Ala Lys Ser Lys Asn Ile

Thr Gly Thr Asn Ile Val Val Asp Asn Gly Leu Ile

Ala

It has been found that polypeptides that have an amino acid sequence having at least 60%, preferably at least 80%, advantageously at least 90% of the amino acids identical to the amino acid sequence of SEQ ID No: 1 and SEQ ID No: 2 lead to the reduction of the compound of Formula (II) or (II″) in the (R) configuration with high yields and high enantiomeric selectivity. In fact, the obtained enantiomeric excess of the compound of Formula (I), (I′) and (I″) in the (R) configuration is at least about 90%, preferably at least about 95% and more preferably at least about 99%. According to an advantageous embodiment of the invention, the cofactor is selected from nicotinamide adenine dinucleotide phosphate (NADP) and nicotinamide adenine dinucleotide (NAD).

The cofactor is preferably in the reaction mixture at a concentration from about 0.01 mM to about 5 mM, advantageously from about 0.05 mM to about 0.5 mM. According to an advantageous embodiment of the invention the co-substrate is a secondary alcohol, preferably a secondary alcohol up to 10 carbon atoms, such as 2-propanol, 2-butanol, 2-pentanol, 4-methyl-2-pentanol, 2-heptanol and 2-octanol, preferably 2-propanol or 4-methyl-2-pentanol, more preferably 2-propanol. According to a preferred embodiment, the co-substrate is present in the reaction mixture from about 10% to about 80% (v/v), more preferably from about 10% to about 50%, advantageously at the rate of 15-25%.

Preferably the process of enzymatic reduction of the compounds of Formula (II) or (II″) is carried out in a solvent, advantageously in the presence of a suitable buffer. The reaction of enzymatic reduction of the invention can be carried out in a mono-phase system or a bi-phase system of the kind of water/organic solvent, according to known techniques. In the latter case, an organic solvent that is not involved in the regeneration of the cofactor can be added to the reaction mixture. Examples of such solvents include diethyl ether, tert-butyl methyl ether, diisopropyl ether, dibutyl ether, ethyl acetate, butyl acetate, heptane, hexane or cyclohexane. Such a solvent can be present at a rate of about 1% to 50% in volume based on the volume of the reaction mixture.

When the enzyme is used as a suspension of native cells, the reaction mixture preferably contains from about 100 to 2000 g cells per kg of raw product that has been produced by the reduction.

The buffer used can, for example, be selected from potassium phosphate buffer or triethanolamine buffer, and can further comprise ions for stabilizing the enzyme, for example a source of magnesium ions. Other additives that can be present in the buffer for stabilizing the enzymes can include a polyol, such as glycerol, sorbitol and the like, sulfur compounds such as 1,4-DL-dithiothreitol, glutathione, cysteine or the like, amino acids and peptides or detergents, such as DMSO.

A preferred stabilizer for the enzyme is a polyol, in particular glycerol, that can be present at a rate of about 10-80%, preferably about 50% by weight based on the weight of the cell suspension.

The oxidized cofactor that is formed during the reduction of the compound of Formula (II) or (II″) is regenerated by oxidation of the co-substrate and the oxidation can also be catalyzed by the oxidoreductase itself. Therefore, a particular practical and economical advantage of the present process is that the oxidoreductase affects both the reduction of the compound of Formula (I), (I′) and (I″) and the oxidation of the co-substrate, and thus it is not necessary to use other enzymes for regenerating the cofactor.

The pH of the reaction mixture, after the addition of all the components, will be between 5 and 10, preferably from 7 to 9 and optimally about 7.5. The enzymatic reduction according to the present invention is carried out at a temperature of about 10-45° C., preferably about 20-40° C., preferably about 35-40° C. The process of enantioselective reduction is convenient and eco-friendly, in addition to providing the alcohols of Formula (I), (I') and (I") with high yields and high enantiomeric selectivity.

The compound of Formula (I), (I') and (I") in the (R) configuration with high optical purity can be obtained in the presence of the oxidoreductase enzyme in the reaction conditions mentioned above in about 2 to 96 hours, preferably from about 4 to 24 hours. During the incubation, the pH of the mixture is preferably maintained within the ranges indicated above. The efficiency of the enantioselective enzymatic reduction can be expressed by the total turnover number (TTN) that is the moles of the chiral alcohol of Formula (I), (I') and (I") produced per mole of cofactor used. The TTN of the enantioselective enzymatic reduction is from about 102 to 105, preferably >103.

According to an embodiment, the at least one oxidoreductase enzyme that is used in the process of the invention, as described above, has a sequence selected from the sequences SEQ. ID No: 1 and SEQ. ID No: 2.

In addition to the sequences SEQ ID No: 1 and SEQ ID No: 2, it has been found that polypeptides that have an amino acid sequence having at least 60%, preferably at least 80%, advantageously at least 90%, identical to the amino acid sequence of SEQ ID No: 1 and SEQ ID No: 2 lead to the reduction of the compound of Formula (II) or (II") in the (R) configuration with high yields and high enantiomeric selectivity. In fact, the enantiomeric excess of the compound of Formula (I) or (I') is at least about 90%, preferably at least about 95% and more preferably at least about 99%. According to a preferred embodiment, subject-matter of the invention is a process of enantioselective reduction of the preferred compounds of Formula (II) and (II"), as reported above, comprising the use of at least one enzyme selected from the sequences SEQ. ID No: 1 and SEQ. ID No: 2 or of polypeptides that have an amino acid sequence having at least 60%, preferably at least 80%, advantageously at least 90%, of the amino acids identical to the amino acid sequence of SEQ. ID No: 1 and SEQ. ID No: 2.

The compound of Formula (I), (I') and (I") can be easily transformed in the corresponding optically active beta-amino alcohol, for example by treating with bases or acids, according to the techniques well known to the person skilled in the art.

Some detailed examples of the reactions described above are reported in the following Experimental section.

Therefore it is understood that, in a completely unexpected way, it has been found that the enzymatic reduction of beta-amino ketones to give optically active beta-amino alcohols, can be carried out provided that the amine group is deprived of its basicity. This fact was not at all conceivable a priori and is an important technical progress in the field of stereoselective reductions.

The compounds of Formula (I), (I') and (I") are versatile synthesis intermediates and can be easily converted to active pharmaceutical ingredients, such as for example adrenalin, noradrenalin, vilanterol, R-salbutamol, R-colterol, R-isoproterenole, (−)-arbutamine and the like.

According to another of its aspects, subject-matter of the invention is a compound of Formula (I) selected from the following compounds:

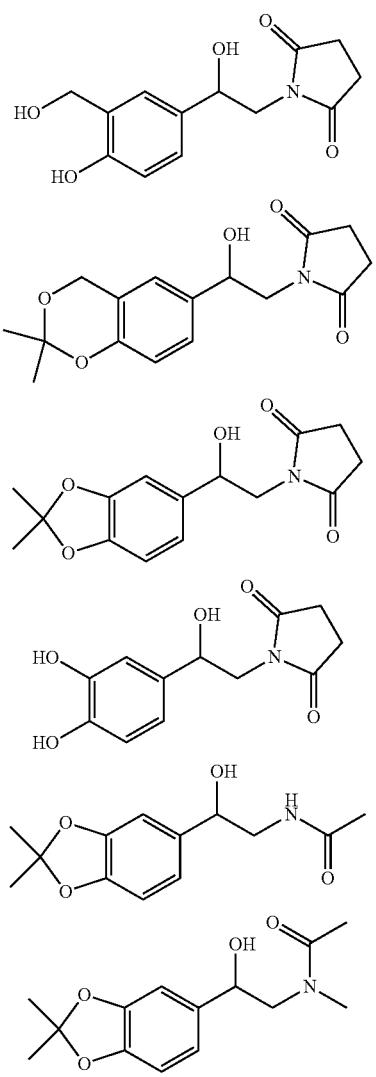

and the salts and/or hydrates and/or solvates thereof.

According to another of its aspects, subject-matter of the invention is a compound of Formula (II) selected from the following compounds:

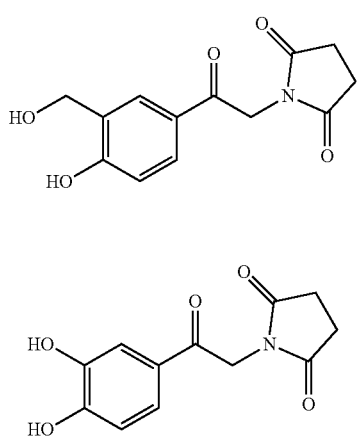

-continued

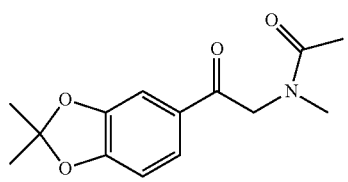

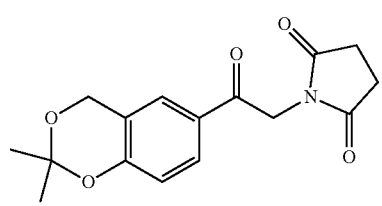

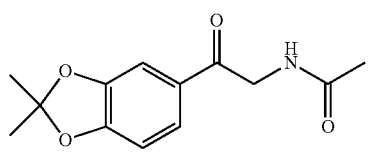

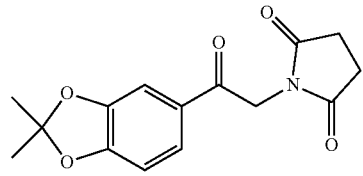

and the salts and/or hydrates and/or solvates thereof.

According to another of its aspects, subject-matter of the invention is the use of at least one compound selected from the compounds of Formula (I), (I'), (I"), (II) or (II") for preparing a compound selected from adrenalin and noradrenalin or one of the salts thereof.

According to another of its aspects, subject-matter of the invention is the use of at least one compound selected from the compounds of Formula (I), (I'), (I"), (II) or (II") for preparing vilanterol or one of the salts thereof.

According to another of its aspects, subject-matter of the invention is the use of the compound having formula B, C

B

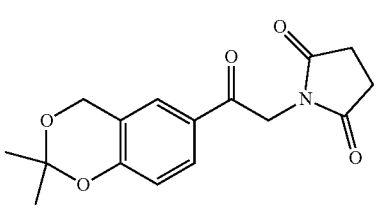

-continued

C

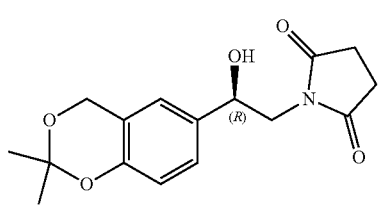

and the salts and/or hydrates and/or solvates thereof, for preparing vilanterol.

According to another of its aspects, subject-matter of the invention is the use of the compound having formula Y, Z,

Y

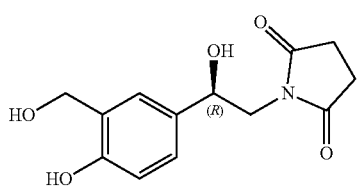

Z

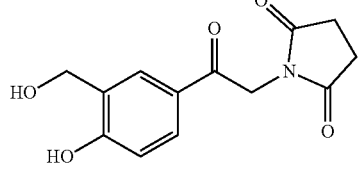

and the salts and/or hydrates and/or solvates thereof, for preparing vilanterol. The examples described in the following Experimental section are provided purely by way of illustration and in no way as limiting.

EXPERIMENTAL SECTION

Abbreviations

DMF=dimethylformamide

DCM=dichloromethane

MTBE=methyl tert-butyl ether

IPA=2-propanol

MP=4-methyl-2-pentanol

THF=tetrahydrofuran

DMS=dimethyl sulfide

Analytic Methods

UPLC purity method (Waters Acquity UPLC™):
  Stationary phase: BEH SHIELD RP18 1.7 µm 2.1×50 mm Column, Mobile phase: $H_2O$+0.05% TFA, $CH_3CN$+0.05% TFA, Gradient: 5% to 100% $CH_3CN$.

Chiral HPLC method (HPLC Agilent 1200):
  Stationary phase: CHIRALPAK AD-H 250×4.6 mm-5*m, Mobile phase: heptane/MeOH/iPrOH 90:5:5+0.1% ethanolamine.

Preparation 1

Preparation of the Enzymatic Solution

Competent *Escherichia coli* cells Starb121 (DE3) (Invitrogen) have been transformed with the construct pET21a-MIX encoding for the oxidoreductases. The colonies of cells transformed with the constructs have been cultured in 200 ml LB medium (1% tryptone, 0.5% yeast extract and 1% NaCl) with 50 µg/ml ampicillin or 40 µg/ml kanamycin, respectively, until an optical density of 0.5 measured at 550 nm is achieved. The expression of the recombinant protein has been induced by adding isopropyl-thiogalactoside (IPTG) with a concentration of 0.1 mM. After 16 hours of induction at 25° C. and 220 revolutions/minute, the cells have been collected and frozen at −20° C. For the preparation of the enzymatic solutions, 30 g cells have been re-suspended in 150 ml triethanolamine buffer (100 mM, pH 7, 2 mM MgCl$_2$, 10% glycerol) and homogenized by using a high pressure homogenizer. Subsequently, the enzymatic solution has been mixed with 150 ml glycerol and stored at −20° C.

Example 1

Preparation of a Compound of Formula (II) and (II")

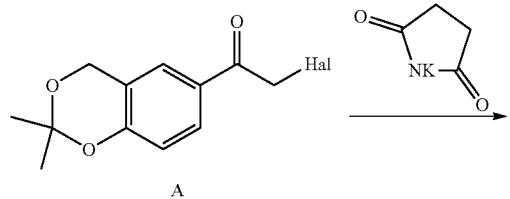

A

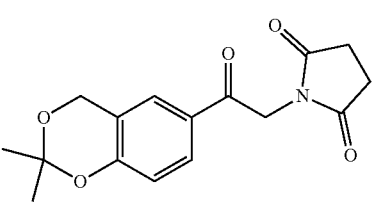

B

Hal=halogen, preferably bromine or chlorine 5 g compound A (wherein Hal=Cl) is dissolved in 50 ml DMF. 3.5 g succinimide potassium salt has been added to the solution. Upon complete reaction, 50 ml water and 100 ml DCM have been added. The organic phase has been dried over sodium sulphate, filtered and concentrated to a residue. 60 ml heptane and 10 ml DCM have been added, then the bulk was filtered, collecting 4.7 g of compound B that, in the dried form, provided 4.5 g of compound B, with HPLC purity higher than 99%.

Example 2

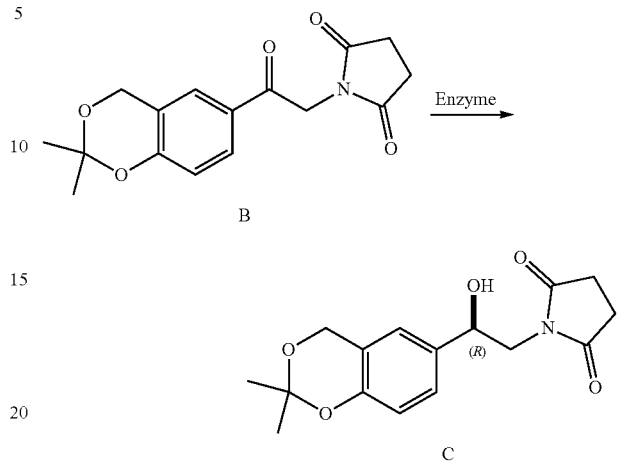

1 g of compound B has been dissolved in 3 ml 2-propanol and 4 ml MTBE. 13 ml aqueous potassium buffer at pH 8, 1 mg NAD and 5 ml enzyme SEQ ID No: 1 (OX 56) have been added. The bulk has been stirred at about 35° C. until complete conversion of ketone to alcohol. The separated aqueous phase has been extracted twice with DCM, then the organic phases have been combined and concentrated to a solid. Yield 900 mg, HPLC purity>96%, S-alcohol not detectable (chiral HPLC analysis).

By operating as described in Example 2, the reactions on compound B and the following compounds have been carried out in the conditions and with the results reported in Table (I):

| Compound | Enzyme | Cofactor | Solvent | ee (S) | ee (R) |
|---|---|---|---|---|---|
| B | SEQ ID No.: 1 (ox56) | NAD | MP | nd | >99.9% |
| D | SEQ ID No.: 1 (ox56) | NAD | IPA | nd | 100% |
| E | SEQ ID No.: 1 (ox56) | NAD | IPA | 0.6% | 99.4% |
| E | SEQ ID No.: 1 (ox56) | NAD | MP | 0.7% | 99.3% |
| F | SEQ ID No.: 2 (ox62) | NAD | IPA | 2.4% | 97.6% |
| F | SEQ ID No.: 2 (ox62) | NAD | MP | 2.0% | 98.0% |
| G | SEQ ID No.: 1 (ox56) | NAD | MP | nd | 100% |
| G | SEQ ID No.: 1 (ox56) | NAD | IPA | nd | 100% |

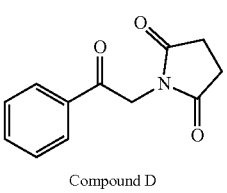 [SMILES: O=C(CN1C(=O)CCC1=O)c1ccccc1]

Compound D

Example 3

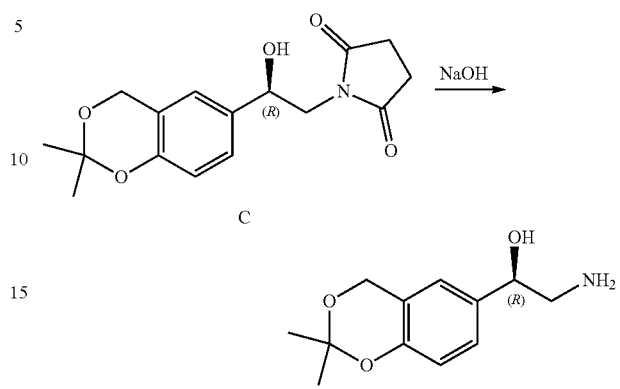

350 mg of compound C has been dissolved in 11 ml ethanol and about 1 g of 20% caustic soda (20 g/100 ml). The bulk has been heated to reflux for about 1 hour. The bulk has been extracted at room temperature with DCM that has been then dried over sodium sulphate, filtered and concentrated to a residue, thus obtaining 210 mg of compound H.

The invention claimed is:
1. A compound selected from the compounds of formula B, C, Y, Z
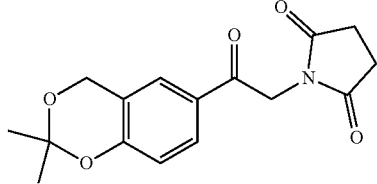
B
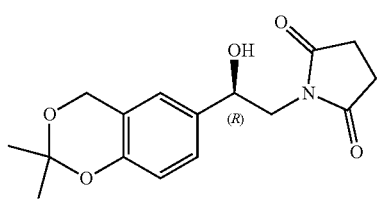
C
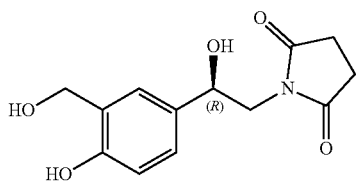
Y
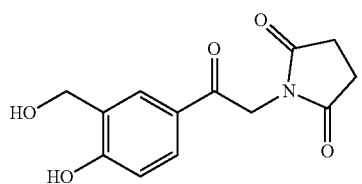
Z
and the salts thereof.
2. A compound of formula B:
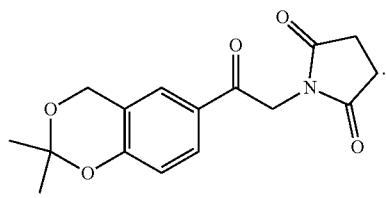
B
3. A compound of formula C:
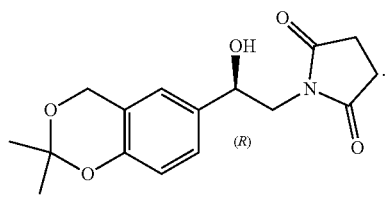
C
4. A compound of formula Y:
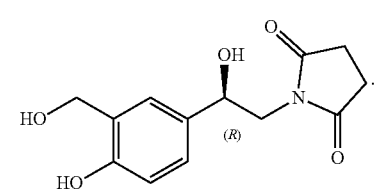
Y
5. A compound of formula Z:
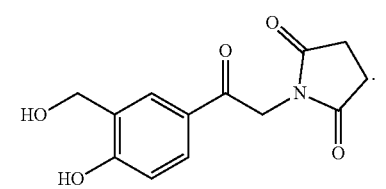
Z
* * * * *